United States Patent [19]

Spolyar

[11] Patent Number: 4,683,582
[45] Date of Patent: * Jul. 28, 1987

[54] PORTABLE ROENTGENOGRAPHIC CEPHALOSTAT

[76] Inventor: John L. Spolyar, 2769 Homewood Dr., Troy, Mich. 48098

[*] Notice: The portion of the term of this patent subsequent to Apr. 1, 2003 has been disclaimed.

[21] Appl. No.: 757,451

[22] Filed: Jul. 22, 1985

Related U.S. Application Data

[63] Continuation of Ser. No. 506,005, Jun. 20, 1983.

[51] Int. Cl.$^4$ ............................................. G03B 42/02
[52] U.S. Cl. ..................................... 378/174; 378/180
[58] Field of Search ............... 378/174, 208, 180, 205; 250/491.1

[56] References Cited

U.S. PATENT DOCUMENTS

| | | | |
|---|---|---|---|
| 2,254,544 | 9/1941 | Plotz et al. | 378/174 |
| 3,072,788 | 1/1963 | Oller | 250/50 |
| 3,293,430 | 12/1966 | Wustner | 378/174 |
| 3,364,352 | 1/1968 | Fry et al. | 378/180 |
| 3,514,606 | 5/1970 | Rabey | 250/65 |
| 3,626,186 | 12/1971 | Allard | 250/50 |
| 3,633,028 | 1/1972 | Marino | 378/174 |
| 3,704,707 | 12/1972 | Halloran | 128/92 EB |
| 3,737,660 | 6/1973 | Ando et al. | 378/180 |
| 3,790,803 | 2/1974 | Phillips | 378/180 |
| 3,916,207 | 10/1975 | Reed | 378/174 |
| 4,088,893 | 5/1978 | Schroeder | 250/451 |
| 4,144,460 | 3/1979 | Norman | 250/451 |
| 4,229,656 | 10/1980 | Iversen et al. | 250/447 |
| 4,256,112 | 3/1981 | Kopf et al. | 128/303 B |
| 4,341,220 | 7/1982 | Perry | 128/630 |
| 4,566,444 | 1/1986 | Spolyar | 250/491.1 |

Primary Examiner—Janice A. Howell
Attorney, Agent, or Firm—Lon H. Romanski

[57] ABSTRACT

A portable cephalostat is shown as having a frame-like base subassembly which provides for an area upon which a patient's head is to rest and a support for supporting locating arms which serve to locate the patient's head in a selected position; the base subassembly provides for the placement of a first film, to be exposed, below the patient's head and for the placement of additional film, also to be exposed, generally to one side of the patient's head and generally parallel to and spaced a first distance from the mid-sagittal plane of the patient's head; provision is also made for the placement of other film, also to be exposed, generally to the same one side of the patient's head and generally parallel to and spaced a second distance from the mid-sagittal plane of the patient's head; further provision is made for the placement of still further additional film, to be exposed, generally transverse to the patient's head and spaced from the top thereof; an indicator is provided for, upon attaining the desired location of the patient's head, automatically indicating the elevation of the axis of the patient's auditory canals with respect to the first film; and certain elements are made to be foldable to conserve space and assist in the transportation of the cephalostat.

16 Claims, 21 Drawing Figures

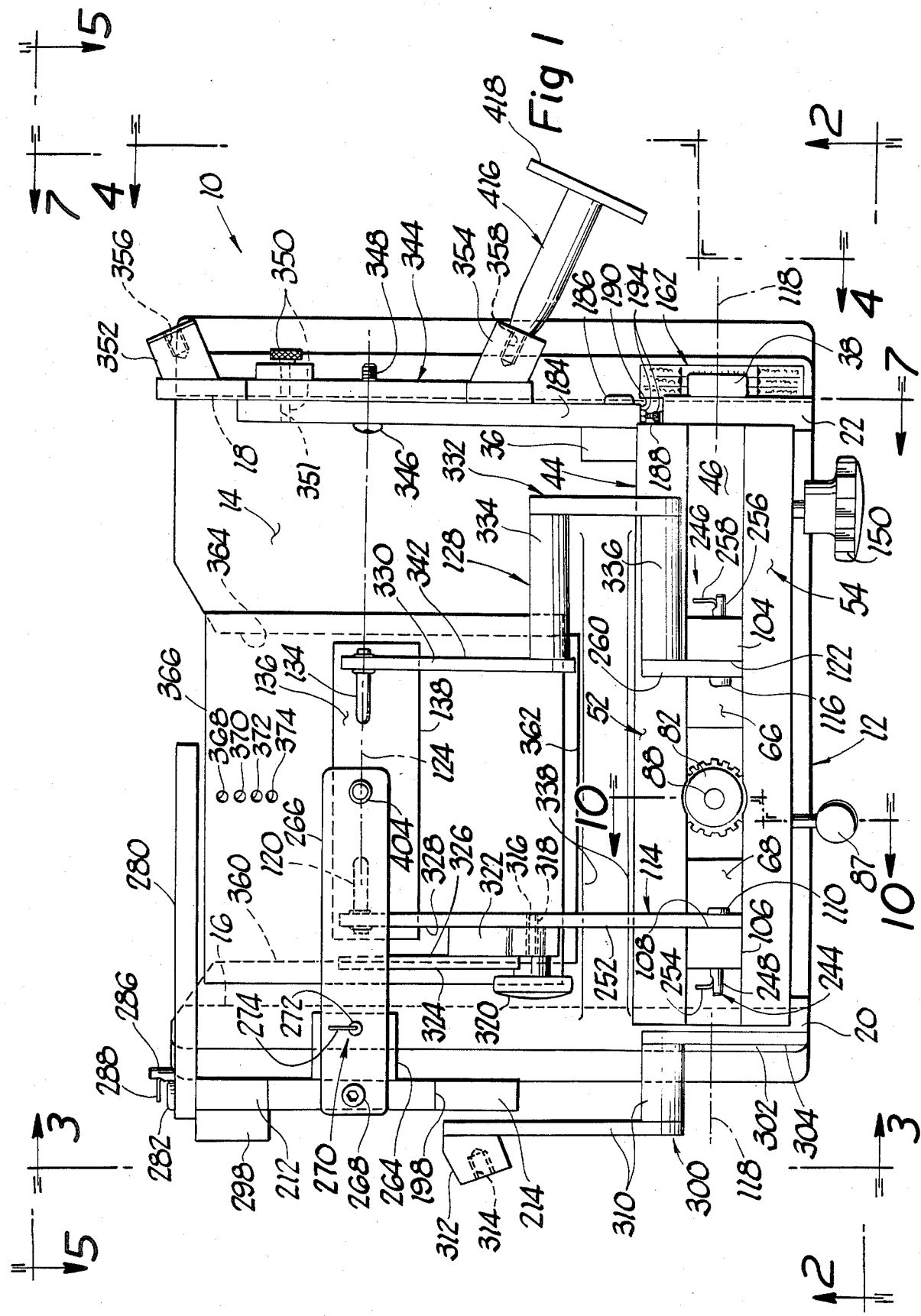

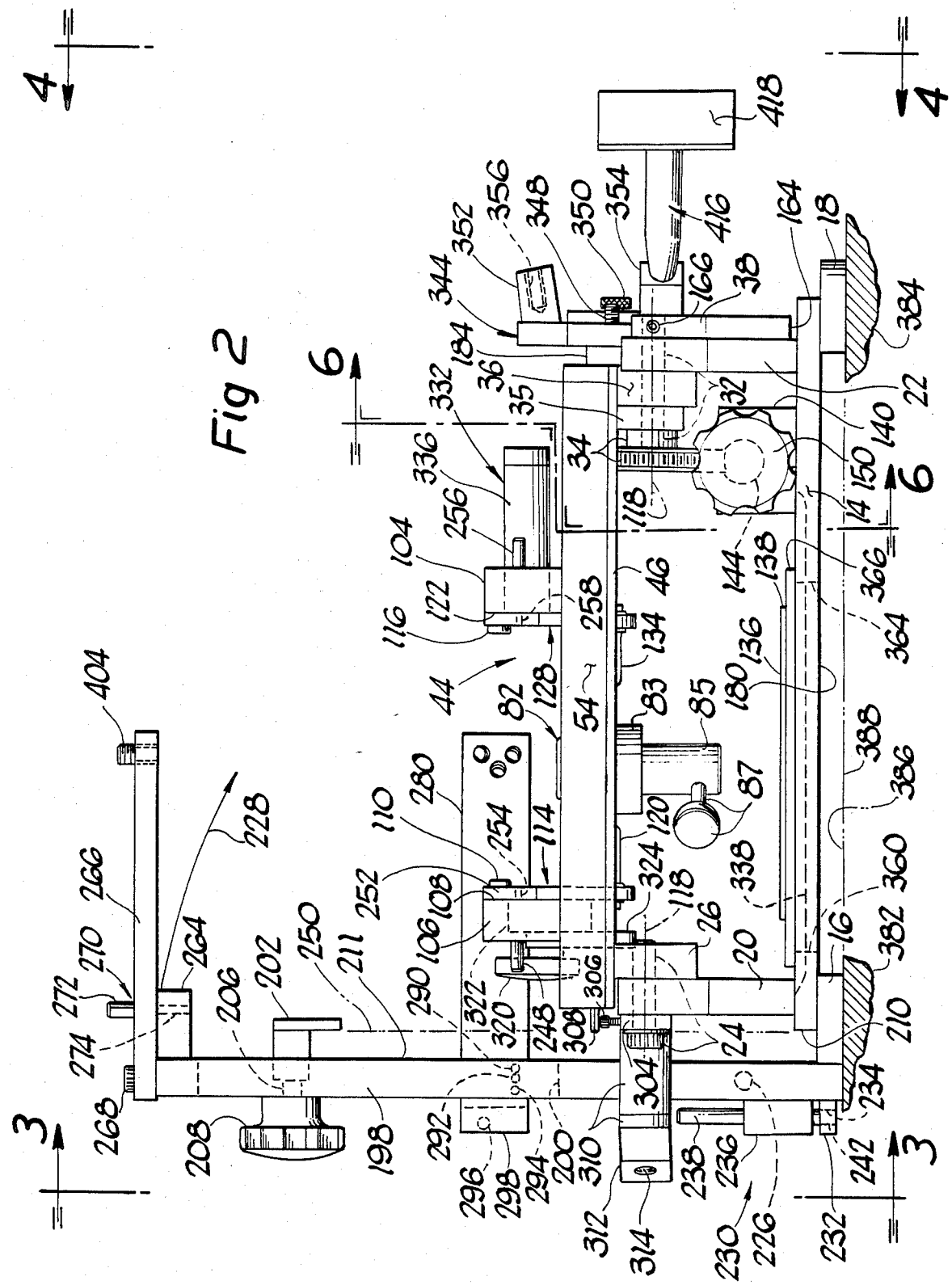

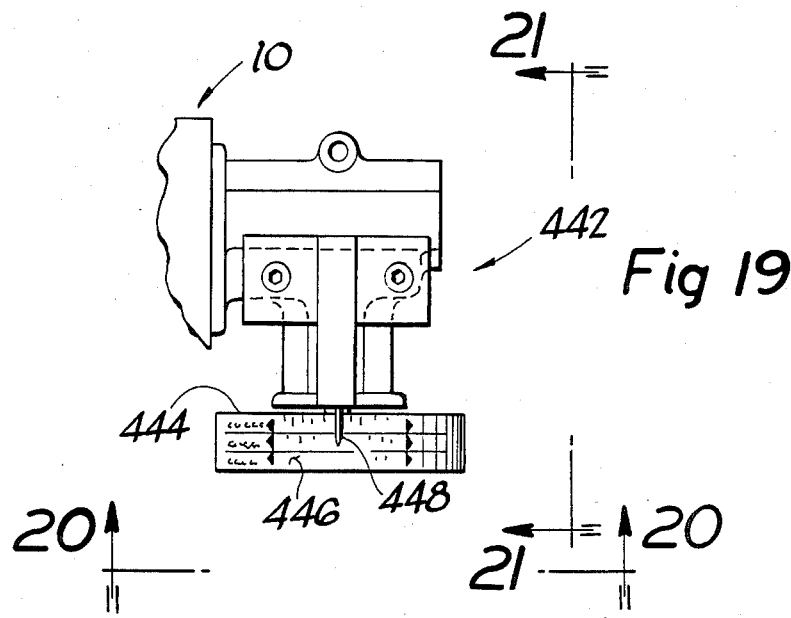
Fig 19
Fig 20
Fig 21
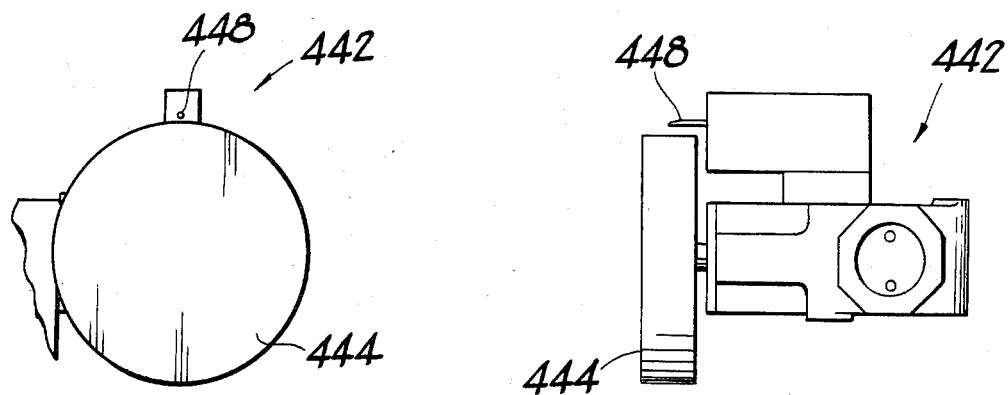
Fig 18

PORTABLE ROENTGENOGRAPHIC CEPHALOSTAT

RELATED APPLICATION

This application is a continuation of my copending application Ser. No. 506,005 filed June 20, 1983, for "Portable Roentgenographic Cephalostat".

FIELD OF THE INVENTION

This invention relates generally to cephalostatic apparatus and more particularly to such apparatus which is portable and enables the production of both lateral and anterior-posterior cephalograms which are reproducible in terms of image magnification and degree of distortions.

BACKGROUND OF THE INVENTION

Heretofore many occassions have arisen where it was at least highly desirable to produce a cephalogram which would have the quality of reproducibility. For example, in the case of orthodontic procedures it is necessary to be able to produce cephalograms, spaced in time, to determine the degree of correction obtained by the procedures employed. If the patient is an infant, or unable to stand or sit in order to be able to have such cephalograms taken by conventional X-ray units designed for this purpose, the practitioner is, more often than not, unable to obtain the required cephalostatic cephalograms and must rely, in the main, upon the visual appearance of the patient or variably magnified and distorted cephalograms which, of course, may be deceiving of the actual situation.

In the instance of oral surgery, for example, if surgery were being performed on the jaw, it would be a distinct advantage for the surgeon to be able to determine the jaw configuration while the patient was still on the operating table. However, the prior art does not provide apparatus permitting such cephalograms to be taken of the patient while still on the operating table.

Further, in cases of cranial surgery, especially where the cranial bone is cut-off during the procedure, as, for example, in infants and young children, for the remediation of early cranial suture closure, it would be of great advantage to the surgeon. That is, it is not uncommon in such procedures to insert bone markers on either side of a bone cut and to periodically thereafter take radiograms to see if the spacing between such bone markers, as well as naturally occuring land marks, has increased indicating displacement growth in the cranial system. It would be of material advantage to the surgeon if a pre-surgical and post-surgical cephalogram could be obtained showing the bone markers and cranial structures while the patient is still on the operating table. Also, such radiograms are difficult to obtain during the patient's convalescence due to patient age and need for sedation to obtain them. Again, the prior art does not provide apparatus enabling such cephalograms to be taken of the patient while still on the operating table or in an X-ray department under sedation.

In all of such exemplory situations, among others, the purpose of the cephalogram is to be able to study and determine changes occurring over a significant span of time in, primarily, the bone structure of the patient. In order to be able to compare a series of such (spaced-in-time) cephalograms, and from that accurately determine what if any changes have occurred, and if occurred, the degree thereof, all variables must be eliminated in the process of obtaining each cephalogram. The prior art has failed to provide such apparatus with such capabilities which, further, could be employed in obtaining cephalograms of infants, invalids incapable of either standing or sitting, or of patients still on the operating table.

The invention as herein disclosed is directed generally to the solution of the above and other related and attendant problems of the prior art.

SUMMARY OF THE INVENTION

According to the invention, a cephalostat comprises portable frame means, first means for locating the back of a patient's head at a reference plane of elevation, second means for locating first unexposed film at a selected elevation below the back of the patient's head and at a preselected elevation below said plane of elevation, third means for locating second unexposed film to one side of the patient's head when the back of said patient's head is located against said reference plane of elevation, mechanically adjustable means for guidingly positioning said patient's head along said reference plane of elevation as to thereby place said patient's head as to have the mid-sagittal plane of said patient's head situated at a preselected distance from said second unexposed film, and additional means for indicating the elevation above said reference plane of elevation of the patient's auditory canals, said third means being foldable as to thereby reduce the overall size of said cephalostat and enhance portability thereof.

Various general and specific objects, advantages and aspects of the invention will become apparent when reference is made to the following detailed description considered in conjunction with the accompanying drawings.

BRIEF DESCRIPTION OF THE DRAWINGS

In the drawings, wherein for purposes of clarity certain details and/or elements may be omitted from one or more views:

FIG. 1 is a top plan view of a cephalostat employing teachings of the invention;

FIG. 2 is a front elevational view taken generally on the plane of line 2—2 of FIG. 1 and looking in the direction of the arrows;

FIG. 18 is a relatively enlarged view of one of the elements shown as in FIG. 1;

FIG. 19 is a generally top plan view of an assembly employable in the practice of a modified form of the invention;

FIG. 20 is a view taken generally on the plane of line 20—20 of FIG. 19 and looking in the direction of the arrows; and FIG. 21 is a view taken generally on the plane of line 21—21 of FIG. 19 and looking in the direction of the arrows;

DETAILED DESCRIPTION OF THE PREFERRED EMBODIMENT OF THE INVENTION

Figure 9:
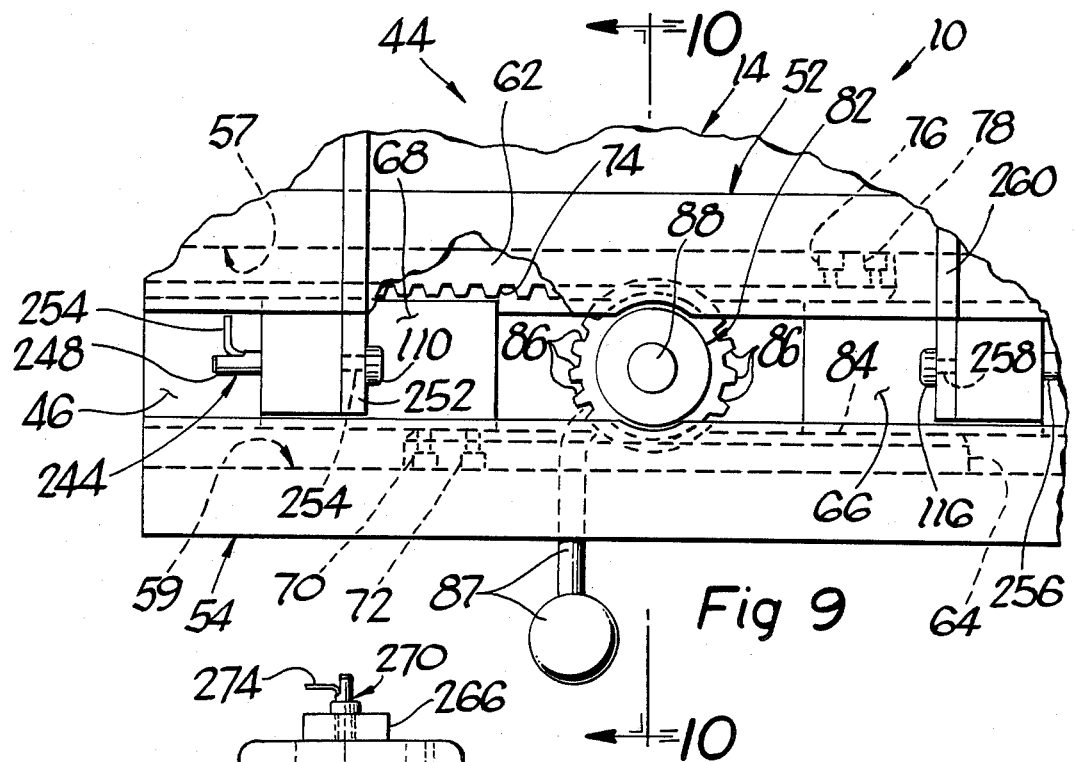
FIG. 9 is a view, relatively enlarged, of a fragmentary portion of the apparatus shown in FIGS. 1, 2 and 3.
Figure 3:
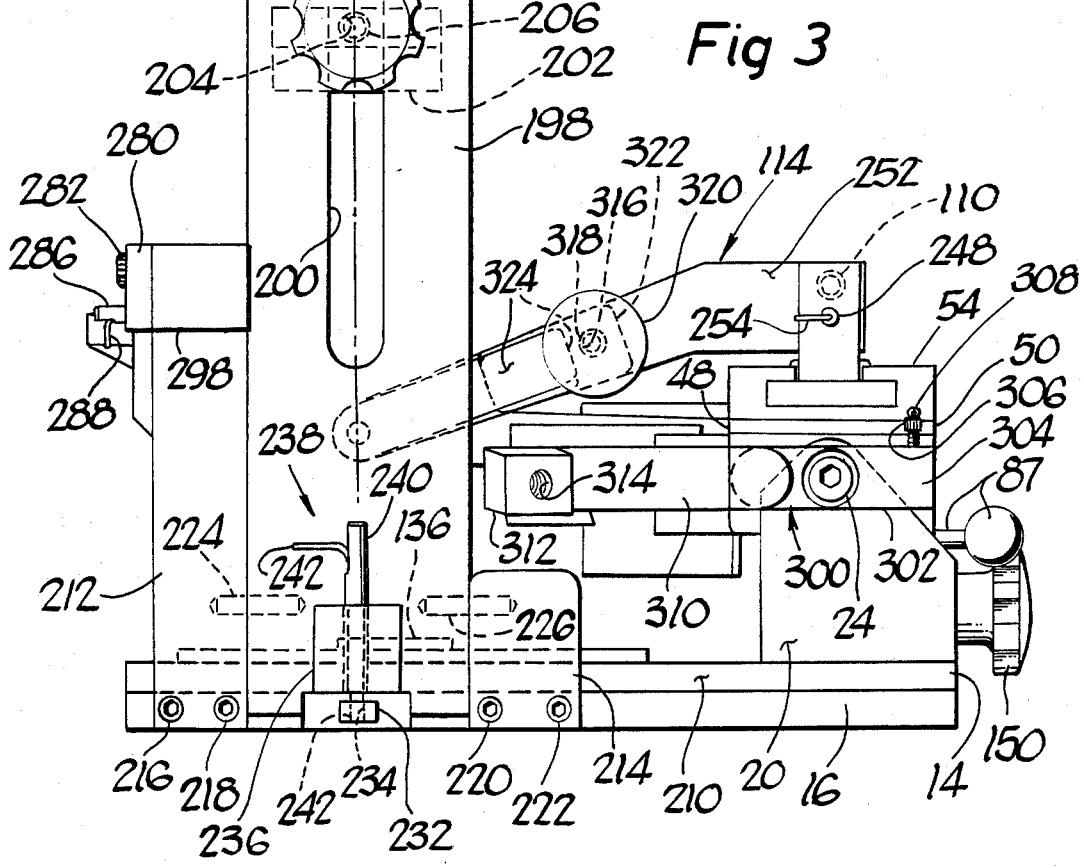
FIG. 3 is an end elevational view taken generally on the plane of line 3—3 of FIG. 1 and looking in the direction of the arrows.

Referring now in greater detail to the drawings, and in particular to FIGS. 1, 2 and 3, the cephalostat 10 of the invention is illustrated as comprising frame or support means 12 which, in turn, preferably comprises a generally rectilinear platelike base 14 which is supported as by parallel spaced legs, risers or feet 16 and 18 which may be integrally formed with or suitably secured to the base 14 by any suitable means such as screws (not shown).

The frame or support means 12 further comprises a pair of generally oppositely disposed trunnion-like or pivot support members 20 and 22 which may be formed of any suitable material but preferably are formed of metal such as, for example, steel. Such pivot support members 20 and 22 may be secured to the base plate 14 in any suitable manner as by, for example, screws (not shown). As shown in, for example, FIG. 2, the support or leg member 20 carries a pivot pin or journal 24 which, in turn, pivotally extends through and supports an associated support block 26. Suitable means may be provided as to axially contain or retain the pivot means 24.

Figure 8:
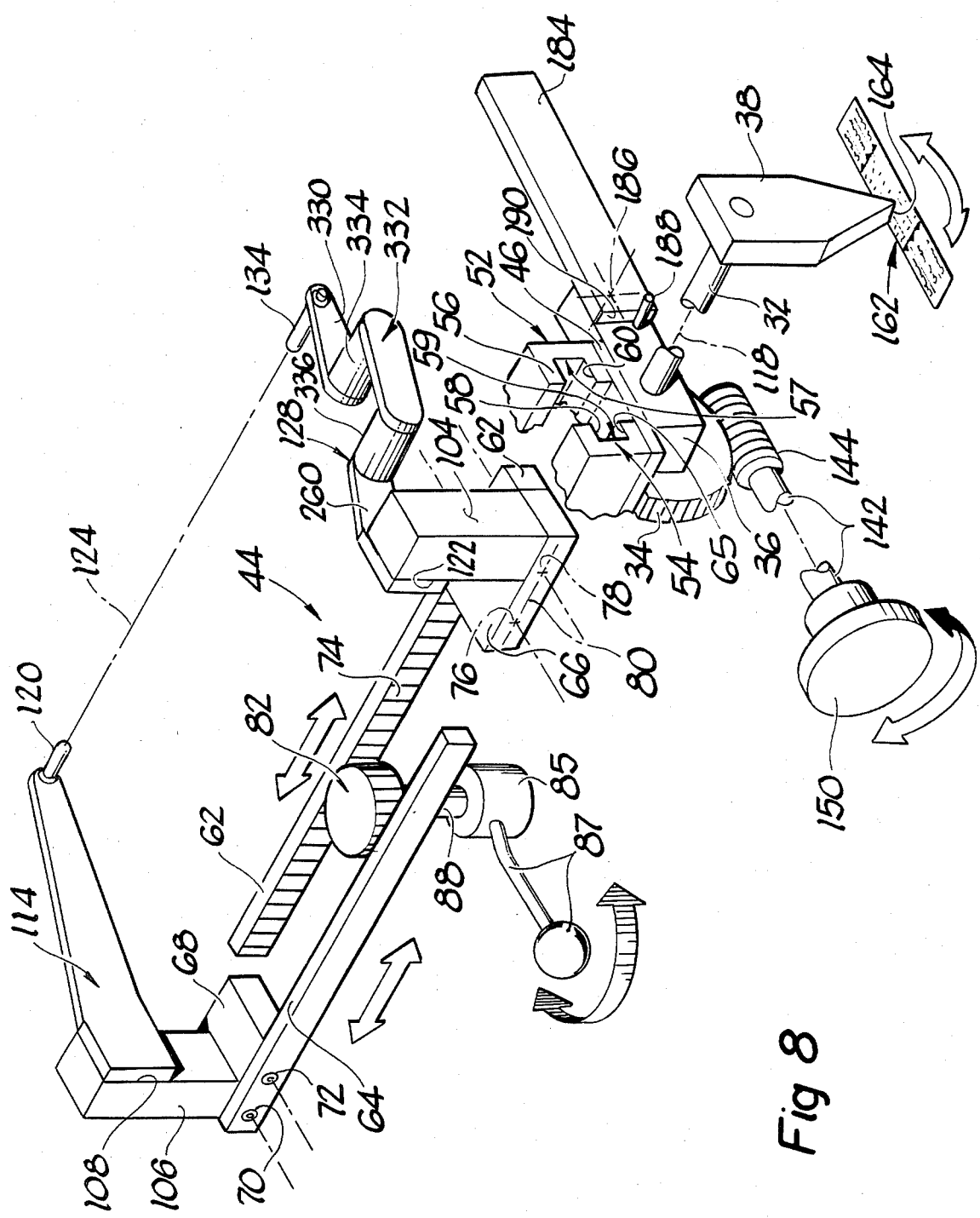
FIG. 8 is a somewhat simplified perspective view of a portion of the operating mechanism shown in FIGS. 1, 2 and 3.

Referring in particular to FIGS. 2, 3 and 8, the support or leg member 22 is shown as pivotally carrying a shaft 32 which, as best seen in FIG. 2, extends to the left (as viewed in FIG. 2) of support member 22 and through associated support block 36, spacer means 35 and worm wheel means 34. As seen in each of FIGS. 1 and 2, the shaft means 32 extends to the right (as viewed in either FIGS. 1 or 2) of support member 22 and into a lever or arm member 38 which is secured thereto for rotation in unison therewith.

In the preferred arrangement, the worm gear 34 and hub portion are pressed or keyed onto shaft means 32 so that rotation of worm gear 34 causes like rotation of the shaft means 32. As generally indicated in FIG. 2, the worm gear 34 may be directly operatively connected to the platform assembly 44 through any suitable means so that rotation of gear 34 results in like rotation of platform assembly 44. Both blocks 26 and 36 are suitably fixedly secured, as by, for example, screws (not shown) to the inclinable platform assembly 44 thereabove.

Referring primarily to FIGS. 1, 2, 8, 9 and 10, the inclinable platform assembly 44 is illustrated as comprising a lower disposed generally rectilinear longitudinally extending base plate member 46 having opposed longitudinal edges 48 and 50 generally along which are situated generally C-shaped (or U-shaped) guides or ways 52 and 54, respectively. Formed integrally with and situated generally at the upper portion of each of the ways 52 and 54 are respective elongated keeper portions 56 and 58, each of a transverse width slightly greater than the ways 52 and 54. The keeper portions, ways and base plate 46 may all be secured to each other, to form a unitary structure, as by screws.

A first gear rack 62 is slidably nested generally within way 52 as to be between upper keeper portion 56 and lower portion 60 as to be slidable longitudinally therealong. A second gear rack 64 is similarly slidably nested generally within way 54 as to be between upper keeper portion 58 and lower portion 65 as to be slidable longitudinally therealong.

As illustrated in, for example, FIGS. 1, 2, 3, 4 and 8 a pair of sliding guide and support blocks 6 and 68 are provided. Slide block 68 sliding generally within recess 57 of way 52 and recess 59 of way 54 is suitably fixedly secured to gear rack 4, preferably by screws 70 and 72 as to thereby move in unison with gear rack 64. In the preferred arrangement, the thickness of slide block 66 may be substantially that of the width of the gear racks 64 and 62 and, further, the width of slide 66 is such as to permit sliding motion as between the teeth 74 of gear rack 62 and the juxtaposed surface of slide 66 whenever such experience relative motion, in, of course, the assembled state depicted as in, for example, FIGS. 1 or 4.

Similarly, slide block 66, sliding generally within recess 57 or way 52 and recess 59 of way 54, is suitably fixedly secured to gear rack 62, preferably by screws entering first through rack 62 and then into slide body 66 with their respective centerlines depicted at 76 and 78 as to thereby move in unison with gear rack 62. In the preferred arrangement, the thickness of slide body 66 may be substantially that of the width of the gear racks 62 and 64 and, further, the width of slide 66 is such as to permit sliding motion as between side or edge 80 of slide 66 and the juxtaposed way 54.

Accordingly, in view of the above, it can be seen that functionally gear rack 64 and slide body 68 are a unitary structure and that when gear rack 64 is made to move longitudinally, slide body 68 moves correspondingly in unison therewith. Further, the same applies to gear rack 62 and slide body 66; that is, such comprise a functionally unitary structure and that when gear rack 62 is made to move longitudinally, slide body 66 moves correspondingly in unison therewith.

Figure 10:
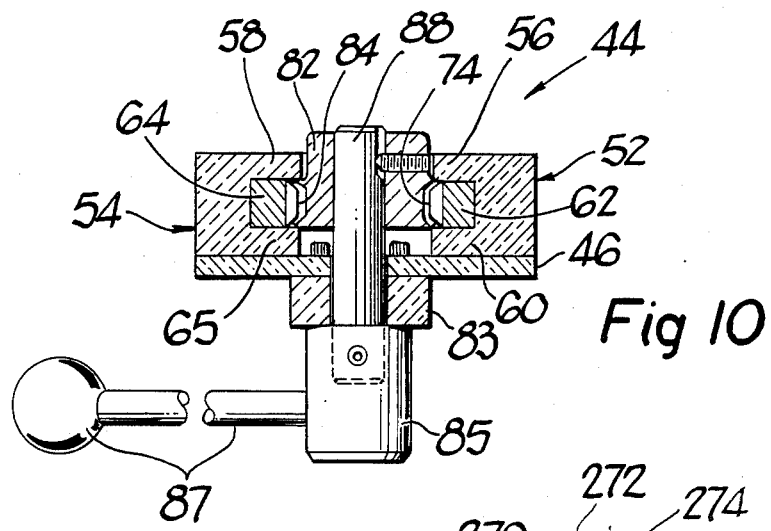
FIG. 10 is a crossectional view taken generally on the plane of line 10-10 of FIG. 9 and looking in the direction of the arrows.

Referring in greater detail to FIGS. 1, 2, 8, 9 and 10, the manner in which such gear racks 62 and 64 are made to move is through a manually actuated gear 82. As possibly best seen in FIGS. 9 and 10, a gear 82 is situated in somewhat abutting engagement with lower surfaces or portions 60 and 65 of thereby preventing its downward movement (as viewed in FIG. 10) and yet slidably rotatable with respect thereto. A keyed shaft 88 extends through the gear 82, through a secured bearing and spacer block 83 as to be fixedly received by a body 85 to which a manually actuatable handle means 87 is secured. As best seen in FIG. 10, the gear 82 is elevationally positioned as to place its teeth 86 in operative engagement, at diametrically opposite sides, with teeth 74 of gear rack 62 and the teeth 84 of gear rack 64.

As should be apparent, rotation of shaft 88 results in the contemporaneous rotation of gear means 82. Further, it can readily be seen that whenever lever means 87 is rotated counter-clockwise (as viewed in either FIGS. 8 or 9) gear rack 62 and slide body 66 move to the left and slide body 68 and rack 64 move to the right; conversely, whenever lever means 87 is rotated clockwise, gear rack 62 and slide body 66 move to the right while gear rack 64 and slide body 68 move to the left.

Consequently, it can be seen, that as knob or control 87 is rotated counter-clockwise, slide blocks or bodies 68 and 66 move linearly toward each other whereas when control means 87 is rotated clockwise, slide blocks or bodies 68 and 66 move linearly away from each other.

It should now be pointed out that the purpose of such slide bodies or blocks 66 and 68 is to support and carry respective support arm members 104 and 106, respectively.

In the construction of the preferred embodiment, such support arm members are fixedly secured to the slide bodies 66 and 68, respectively, prior to the assembly of such slide bodies into and generally between ways 52 and 54. More particularly, referring to FIG. 1, 2, 3, 8 and 9, the support member 106 is illustrated as being situated atop slide body 68, and secured thereto as by a pair of screws (not shown but preferably) extending upwardly from countersunk holes in slide body 68 and into arm member 106 to thereby fixedly secure each to the other and make such secured elements effectively of unitary structure. In the preferred embodiment, the width of arm support 106 is such as to somewhat overlie and slide upon the gear racks 64 and 62. A generally cantilevered locating arm member 114 is preferably fixedly pivotally secured to the support arm 106, against surface 108, and pivotally retained as by shoulder-like pivot means 110. The free end of locating arm 114 fixedly carries a generally cylindrical locating plug 120 of a preselected effective overall length.

Support arm 104, similarly, is situated atop slide body 66, and secured thereto as by a pair of screws (not shown but preferably) extending upwardly from countersunk holes in slide body 66 and into arm member 104 to thereby fixedly secure each to the other and make such secured elements effectively of unitary structure. The arm member 104 may be considered the mirror image of arm 106. Also, similarly, support arm 104 may be of a width as to somewhat overlie and slide against the gear racks 64 and 62. A generally cantilevered locating arm structure 128 is preferably fixedly pivotally secured to the support arm 104 as against surface 122, and pivotally retained as by shoulder-like pivot means 116. The free end of locating arm 128 carries a locating member 134 of preselected effective length which, preferably, is the same as that of locator 120.

The entire platform assembly 44 can be pivotally rotated about the aligned axes of pivot pin 24 and shaft means 32 and in so doing the height of the aligned centerlines of locators 120 and 134 is effectively raised or lowered relative to the reference plane 136 comprising the top surface of the head riser or locator member 138 upon which the back of the patient's head is to rest. Of course, such upward and downward movement of the locators 120 and 134 is in an arcuate path with the radius of such arcuate path being the distance from the aligned axes 118 of pivot pin 24 and shaft means 32 to the aligned axes 124 of locators 120 and 134.

Figure 6:
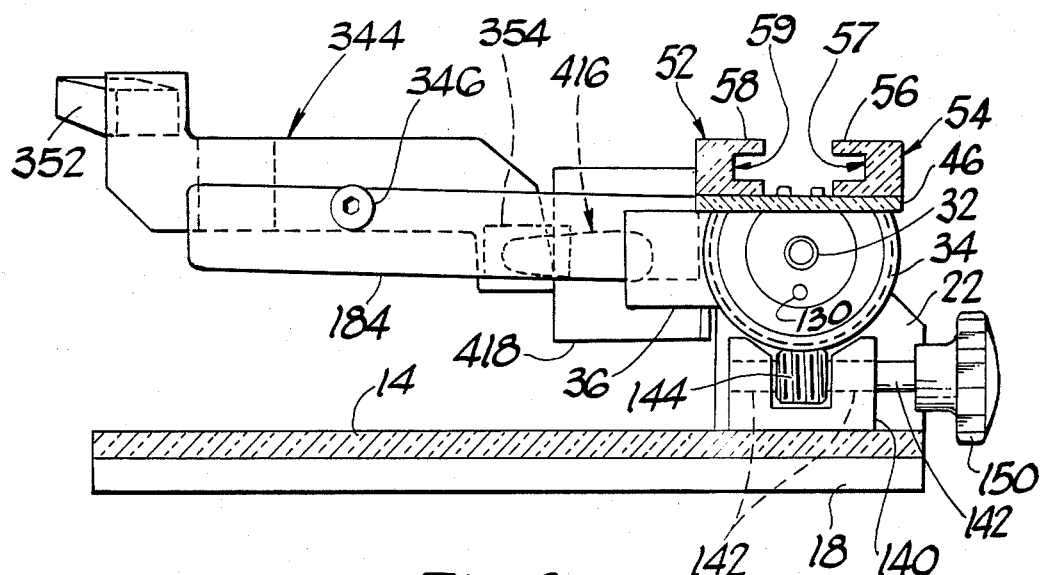
FIG. 6 is a relatively enlarged, generally cross-sectional view, taken generally on the plane of line 6—6 of FIG. 2 and looking in the direction of the arrows.

Referring primarily to FIGS. 2, 6, 7 and 8, the manner and means by which the platform assembly 44 is controllably pivotally rotated about pivot pin 24 and shaft means 32 is generally as follows. That is, as depicted in FIGS. 2 and 6, a worm shaft support block 140 is suitably fixedly secured as to the base member 14 and, in turn, journals a shaft means 142 fixedly carrying a worm shaft 144. One end of the shaft means 142 may be secured to a knob 150 as by a press-fit effectively locking the shaft means 142 to the knob 150.

As was previously described, block 36 (FIGS. 2 and 5) may be secured as by screws, to the platform base 46 and also to the worm gear 34 for unitary motion therewith. Accordingly, if the adjustment knob 150 is rotated, for example, clockwise the resulting rotating worm shaft 144, engaged with worm gear 34, causes worm gear 34 to rotate in a clockwise direction (as viewed in either FIGS. 4, 7 or 8). Since block 36 may be considered as driven by worm gear 34, and may be secured to platform base 46, such rotation of worm gear 34 causes a swingable rotation of the platform base 46 and, in fact, the entire platform assembly 44 in a clockwise direction (as viewed in either FIGS. 4, 7 or 8). As a further consequence of such a swingable rotation (clockwise as viewed in either FIGS. 4, 7 or 8), the free ends of locating arms 114 and 128 swing generally downwardly toward the plane 136.

If the adjustment knob 150 is rotated counter-clockwise the resulting rotating worm shaft 144, engaged with worm gear 34, causes worm gear 34 to rotate in a counter-clockwise direction. Since block 36 may be considered as driven by worm gear 34, and may be secured to platform base 46, such rotation of worm gear 34 causes a swingable rotation of the platform base 46 and, in fact, the entire platform assembly 44. As a further consequence of such a swingable rotation of the platform assembly 44, the free ends of locating arm means 114 and 128 swing generally upwardly away from the plane 136.

As shown in FIGS. 1, 2, 4, 5 and 8, a pointer or indicator means 38 is fixedly secured to shaft means 32, as by a set screw 166, and comprises a swingable pointed portion 164 which passes rather closely to a related gauging means or scale 162 which may be carried as by the upper disposed surface of plate-like base member 14.

As previously described, rotation of knob 150 causes, as its ultimate purpose, the relative raising or lowering of the locators 120 and 134 (and the coaxial axes thereof). During such upward and downward movement of the locators 120 and 134, shaft means 32 is also undergoing rotation and such rotation is conveyed to pointer or indicator means 38 which undergoes rotation in unison with the rotation of platform assembly 44 and locators 120 and 134. As the indicator means 38 is thusly caused to generally arcuately sweep above, and yet in juxtaposition to said gauging or scale means 162, the pointer end 164, when viewed in its general juxtaposed position to the said means 162 serves to indicate, to the operator, the actual elevation of the common axis of locators 120 and 134 above the lower reference surface or plane 136. For example, if through such rotation of knob 150, the common axis 124 of locators 120 and 134 is brought to a then selected position, and, let it be assumed, the pointer portion 164 of the indicator means 38 is juxtaposed to a numeral "11" on the scale or guage means 162, then this, in the preferred embodiment, indicates to the operator that the actual elevation, of the common axis 124 of locators 120 and 134, is 11.0 cm. above the lower surface 180 of base plate 14. Similarly, if pointed portion 164 was seen to be juxtaposed or aligned with a graduation or designation identified as either "6", "7", "8", "938, "10", "12", "13", "14", "15", or "16", such would indicate to the operator that the actual elevation or distance of the common axis 124, of locators 120 and 134, to the bottom or lower surface 180 of base plate 14 would be, respectively: 6.0 cm., 7.0 cm., 8.0 cm., 9.0 cm., 10.0 cm., 12.0 cm., 13.0 cm., 14.0 cm., 15.0 cm. or 16.0 cm.

Figure 4:
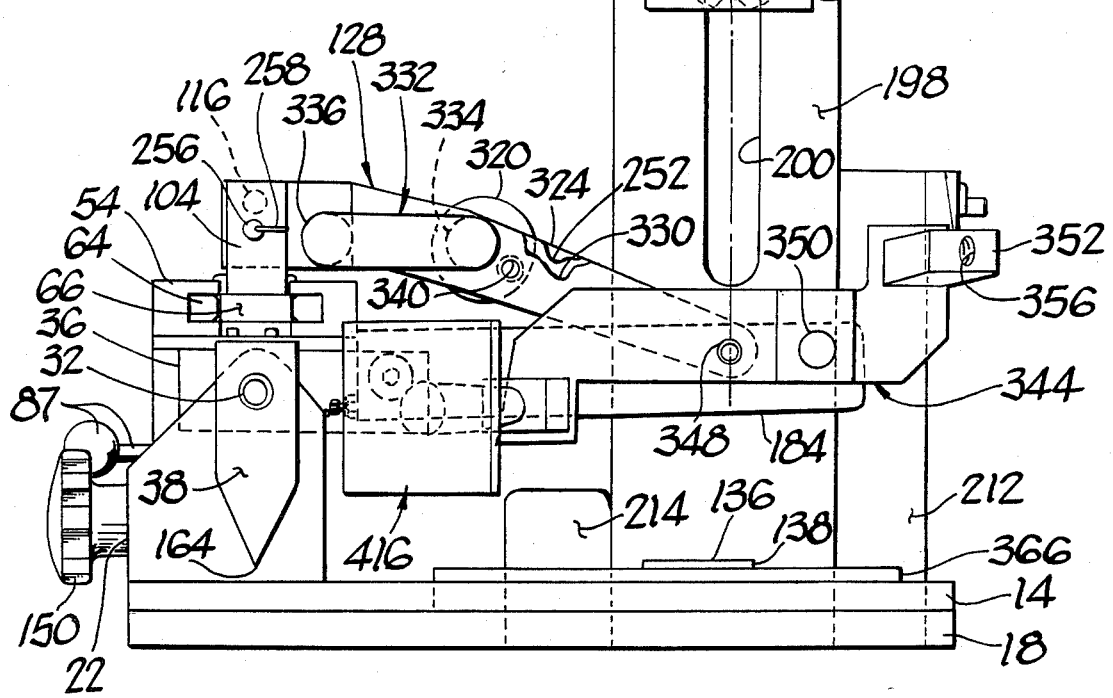
FIG. 4 is an end elevational view taken generally on the plane of line 4—4 of FIG. 1 and looking in the direction of the arrows.
Figure 7:
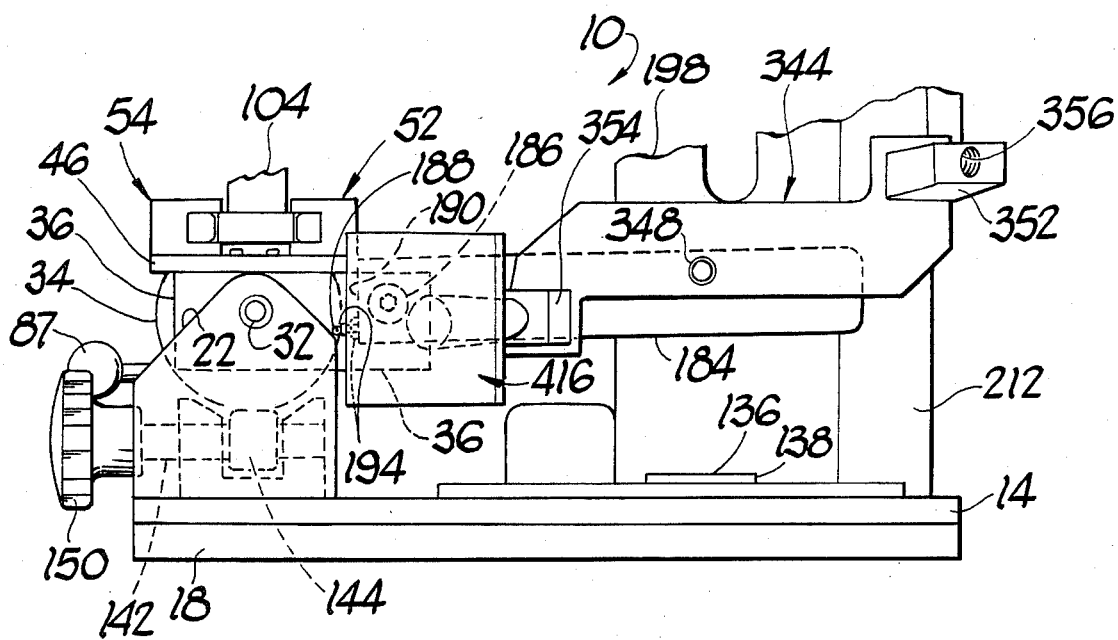
FIG. 7 is a view taken generally on the plane of line 7—7 of FIG. 1 and looking in the direction of the arrows.

As possibly best seen in FIGS. 4, 7 and 8, the block 36, which may in fact be keyed, as by suitable keying means 130, to gear 34, preferably extends beyond the platform assembly 44 and has a support arm or member 184 secured to block 36 as by a retainer and pivot member 186. An abutment which, for example, may take the form of a metal rod 188 or the like, is carried by lever or block 36 and serves as a stop against which the generally lower part of end-edge 190 of adapter arm 184 abuts when permitted to rotate clockwise (as viewed in FIG. 7) about pivot 186. In order to provide for a degree of adjustment to assure that when adapter arm 184 is thusly in abutting engagement, that its relative position will be that as desired, a threaded member 194, such as a screw or the like, may be carried by the adapter arm 184 and threadably axially adjusted as to cause such member 194 to abut against stop 188 and, through such adjustment, attain the desired relationship as, for example, locators 120, 134 and reference apertures or surfaces positioned or positionable by support arm 184. Obviously, adapter arm 184, through its connection to shaft 32 and gear 34 rotates in unison with platform assembly 44 and locating arms 114 and 128.

At the left end, as viewed in FIGS. 1 and 2, a generally vertically upwardly extending plate or support member 198 is suitably secured to the frame or base means 12. As best seen in FIGS. 1 and 4, such support plate 198 may be comparatively rather narrow and is provided with a generally medially situated elongated slot 200. A clamp 202, which may be generally guided by the slot 200, is provided with a threaded passage portion 204 which threadably receives a threaded shank portion 206 of a manually actuatable knob 208. In the preferred arrangement, the distance from edge 210, of plate 14, to the inner surface 211 of plate 198 is such as to closely receive therein a film cassette 250.

In the preferred embodiment, the vertically extending plate or support 198 is pivotally supported by trunnion or support blocks 212 and 214 which are oppositely disposed about plate 198 and fixedly secured to the base, frame or body means 12 as by screws 216, 218, 220 and 222. Pivot members 224 and 226 respectively carried by supports 212 and 214 are operatively engaged by vertical plate 198 and permit the rotation of support plate 198 thereabout. The rotation, to a folded position, of support plate 198 would be generally clockwise about the axis of pivots 224 and 226 as viewed in FIG. 2 and as generally depicted by arcuate arrow 228. When in a completely folded condition, support plate 198 would be in a generally horizontal position generally overlying the base plate means 14.

In the preferred embodiment, the vertical member 198 is maintained in its vertical position by a locking or latching means 230. More particularly, the latching means 230 is illustrated as comprising a relatively lower disposed body portion 232 fixedly secured, against movement, as to, for example, leg 16, and having a recess or aperture 234 formed therein. The latching means 230 is further comprised of a body 236, fixedly secured to the plate 198, which carries a spring-loaded plunger assembly 238 which, in turn, is comprised of a plunger housing 240, guidingly containing the plunger member 242 and the spring means urging such plunger member 242 downwardly into cooperative engagement with passage or aperture 234. All that need be done in order to fold support 198 is to raise plunger 242 (as viewed in FIG. 3) thereby raising the lower end of 242 out of engagement with aperture or recess 234 and then rotating support 198 about the axis of pivots 224 and 226 in the direction of arrow 228 of FIG. 2. Obviously, when subsequently raised to a vertical position, the plunger 242 is operatively engaged with recess 234 in order to maintain the support 198 in such a vertical position As is apparent from an inspection of both FIGS. 1 and 2, if vertical support 198 were to be pivotally rotated to a folded position, as hereinbefore described, arm structures 114 and 128 would interfere in such pivotal movement of support 198. Therefore, to overcome such a problem, arm means 114 and 128 are respectively pivotally mounted by pivot means 110 and 116 and, further, are respectively provided with latching means 244 and 246 each of may be functionally similar to latching means 238.

Referring to FIGS. 1, 2 and 3, in the preferred embodiment, latching means 244 comprises a plunger body or housing 248, fixedly secured to and carried by support block 106, guidingly containing a plunger member 254 and spring means urging such plunger member 254 into cooperative engagement with a passage or aperture formed in arm portion 252.

Similarly, latching means 246 comprises a plunger-body or housing 256, fixedly secured to and carried by support block 104, guidingly containing a plunger member 258 and spring means urging such plunger member 258 into cooperative engagement with a passage or aperture formed in arm portion 260.

When spring-loaded plunger 254 is withdrawn from the cooperating aperture or passage in arm portion 252, arm means 114 can be pivotally rotated about pivot means 110. Also, when spring-loaded plunger 258 is withdrawn from the cooperating aperture or passage in arm portion 260, arm means 128 can be pivotally rotated about pivot means 116. Consequently, when it is desired that support 198 be folded, spring loaded plungers or retainers 254 and 258 are first withdrawn from their respective locked or latched positions and arm means 114 and 128 are pivotally rotated clockwise (as viewed in FIG. 3) until the respective swinging ends thereof reach a position where they are out of the path of movement of the vertical support 198 while in its subsequent pivotal motion toward a folded condition. After the support 198 is thusly folded, arm means 114 and 128 may be returned to their respective original positions and latched as by the plunger members 254 and 258 again being respectively received in the cooperating apertures or passages in arm portions 252 and 260, respectively.

The top of support 198 is provided with a block or body portion 264 fixedly secured thereto by any suitable means. A swingable arm 266 is pivotally secured, as by pivot and retainer means 268, to the top of support 198 and, further, carries a latching means 270. Latching means 270 comprises a plunger body or housing 272, fixedly secured to and carried by arm 266, guidingly containing a plunger member 274 and spring means urging such plunger member 274 into cooperative engagement with a passageway or aperture formed in body 264 so as to maintain the arm 266 in the position depicted in FIG. 1. When the plunger or retainer member 274 is withdrawn from the cooperating passage or aperture, arm 266 may be pivotally rotated about pivot means 268 in either the clockwise or counter-clockwise direction as viewed in FIG. 1. Obviously, when vertical support 198 is moved to a folded position as hereinbefore described, latching member 274 would be first withdrawn thereby permitting arm 266 to be swung to accommodate the horizontal attitude of the folded support 198.

Figure 5:
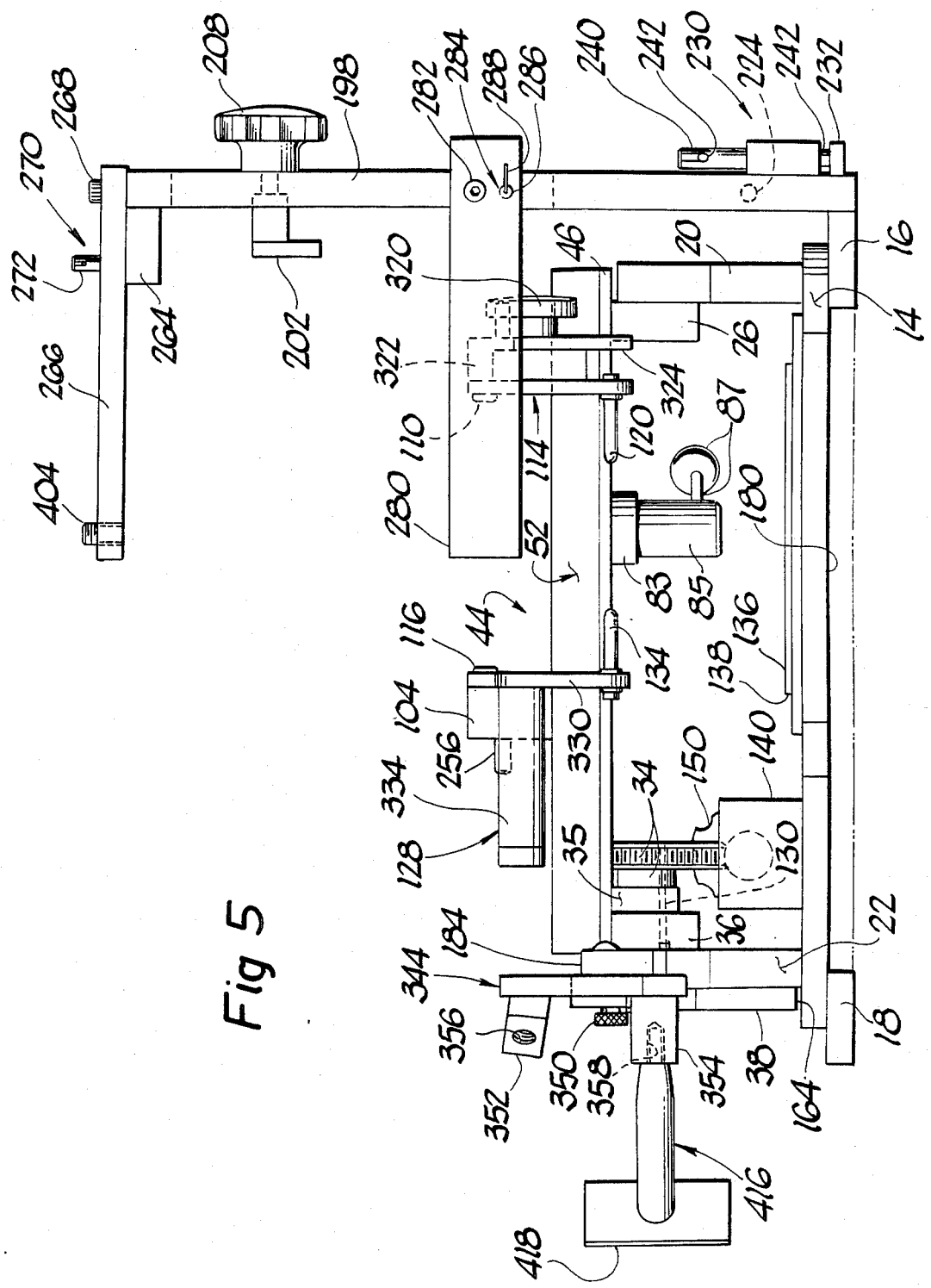
FIG. 5 is an elevational view taken generally on the plane of line 5—5 of FIG. 1 and looking in the direction of the arrows.

A further arm 280 is pivotally secured to the trunnion or support member 212 as by a pivot and retainer member 282. As generally depicted in FIGS. 1, 2 and 5, arm 280 carries a latching means 284 which comprises a plunger body or housing 286, fixedly secured to and carried by arm 280, guidingly containing a plunger member 288 and spring means urging such plunger member 288 into cooperative engagement with either of passageways or apertures 290, 292 and 294 formed as within trunnion or support 212. A fourth passageway or aperture 296 may be in block or body 298, fixedly secured to trunnion member 212, for use in receiving the plunger 288 and thereby hold arm 280 in a folded out-of-the-way position Such apertures or passages 290, 292, 294 and 296 are best illustrated, in hidden line, in FIG. 2.

As shown in each of FIGS. 1, 2 and 3 an arm means 300 is pivotally mounted, as by the pivot means 24 to the trunnion or pedestal support 20. In the embodiment disclosed, the arm means 300 comprises an arm body portion 302 through which the pivot means 24 extends and which, when viewed as in FIG. 3 has a relatively short lever arm portion 304 carrying a threadably adjustable screw means 306, or the like, which is intended to abut against a stop member 308 carried as by the rack way 54. The other lever arm portion 310 is generally off-set, as viewed in FIG. 1, thereby preventing any interference as between, for example, supports 214, 198 and end portion 312 of lever arm 310. The end portion 312 is preferably provided with a threaded aperture 314 the axis of which forms a selected angle with, for example a vertical plane passing through axis 124. Generally, arm 300 is able to rotate in a plane parallel to the midsagittal plane and about the axis of rotation 118 of the arm means 114 and 128. An adaptive bracket may then be attached as by cooperative engagement with threaded aperture 314 to orient the X-ray head of an associated X-ray machine when taking an X-ray of the patient's right temporo-mandibular joint. Generally, the arm 300 is parallel to the base of the apparatus 10 and any required fine adjustments can be made by means of the threadable adjustment means 306.

In the preferred embodiment arm portion 252 of arm means 114 is provided with a threaded aperture 316 which threadably receives a threaded shank 318 fixedly secured to a knob 320 for rotation in unison therewith. A spacer-like body portion 322, having a cantilevered-like arm 324, receives the shank 318 therethrough. When the knob 320 is pressed against body 322 and the shank 318 is tightly engaged with aperture 316, the resulting space defined between juxtaposed surfaces 326 and 328, of arm 324 and 252, serves to receive and hold a cassette of film (to be exposed by X-ray) if such placement of the film is desired by the operator. This, in effect, would result in a second generally vertical location of film, to be exposed, which is parallel to the film held by the vertical support 198 but at a distance closer to the patient's mids-agittal plane.

As possibly best shown in FIGS. 1 and 8, in the preferred embodiment the arm means 128 is comprised of arm portions 260 and 330 which are operatively joined or connected to each other as by a generally U-shaped (as viewed in FIG. 1) intermediate arm portion 332 having, what may be considered, leg portions 334 and 336. The U-shaped eccentric portion 332 of arm means 128 is of a size, and the space between leg portions 334 and 336 is such as to accommodate the placement of a film cassette, of film to be exposed. The film and cassette would be generally parallel to the axis 124, located near the top of the patient's head, and be intended for X-ray exposure generally in a direction which would be as if one were viewing the patient's head from under the patient's chin and toward the top of the patient's head. In the preferred arrangement, this would result in the film cassette being inclined in the order of 6° from the vertical with the top of the film cassette being tilted away from the patient's head. Generally, this would be known as a sub-mental-vertex radiogram. Further, the provision of such an eccentric portion 332 enables the necessary angular and translational adjustment of arm means 128 without in any way adversely effecting the film cassette placed in such slot (between legs 334 and 336) which, of course, continue to serve as a film cassette holder or stabilizer.

In the preferred embodiment a lower receiving or retainer means is also provided for the film cassette generally contained by leg portions 334 and 336. More particularly, as generally depicted in FIGS. 1 and 2, preferably, an elongated slot or recess 338 is formed as in the base plate means 14. Such slot means 338 would be generally parallel to the axis 124 and of a width and length sufficient to hold an edge of a film cassette. By way of example, the slot or recess means 338 may be in the order of 3/16 inch deep.

As shown in FIG. 4, arm portion 330 of arm means 128 is provided with a threaded aperture 340 corresponding in size to threaded aperture 316 of arm portion 252. The purpose of threaded aperture 340 is the same as that of threaded aperture 316 and that is to be threadably engaged with shank 318 and support spacer 322 and arm 324. More specifically, in certain situations, the operator may want to position the film and film cassette to the right side of and close to the patient's head. This can be easily achieved by disengaging knob 320 and threaded shank 318 from lever or arm portion 252 then placing the spacer against surface 342 of arm portion 330 and threadably engaging shank 318 with threaded aperture 340. The space then between juxtaposed surface 326 of arm 324 and surface 342 of arm portion 330 serves to hold the film and film cassette. Generally, the film and film cassette would be thusly situated between juxtaposed surfaces 342 and 326 when the direction of the X-ray radiation or exposure would be in general axial alignment with aperture means 314 of arm or locator means 300 hereinbefore described.

As briefly referred to and as depicted in, for example, FIGS. 1, 4, 5, 6, 7 and 8, a locator or support arm 184 is carried by member 36. A second locator or alignment member 344 is carried by support arm 184 as by a retainer and pivotal support 346 which may have a threaded shank portion 348. In the preferred embodiment the axis of pivot retainer means 346 and axis 124 are coincident. This can be established as by adjustment means 194 and 188. Further, as generally depicted in FIGS. 1 and 4, a spring loaded detent or plunger means 350 is carried by lever means 344 and engageable with a cooperating passage or aperture 352 formed in support arm 184 thereby establishing a selected relative relationship. As should now be evident, as knob 150 is turned to arcuately raise or lower arm means 114 and 128, and locators 120 and 134, support arm 184 is rotated in unison and carries lever or locator means 344 with it.

As depicted in, for example, FIGS. 1, 2, 4, 5 and 7, locator means 344 comprises block or body portions 352 and 354 which respectively have threaded apertures 356 and 358 formed therein.

As possibly best depicted in FIGS. 1 and 2, in the preferred embodiment an area or portion defined by edges 360, 362 and 364 is removed from the relatively thick (possibly in the order of 0.50 inch) base plate 14. A relatively thin support 366 (possibly in the order of 5/16 inch) of plexiglass or the like is laid across such opening and this, in turn, may carry a second narrow and thin strip 138 of plexiglass, upon which the patient's head would rest, establishing the reference plane 136. In the main, the purpose of reducing the thickness of the head support means 366 and 138 is to reduce to a minimum the attenuation of the X-ray radiation as to the film below the patient's head.

Figure 11:
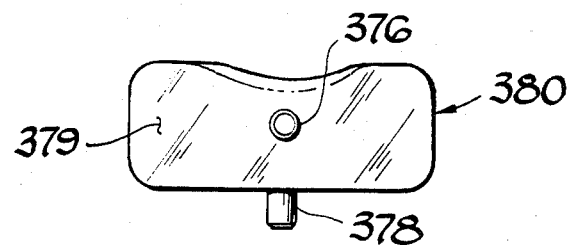
FIGS. 11, 12 and 13 illustrate a head-rest member, employable in practicing the invention, shown, in FIGS. 12 and 13 as in combination with a fragmentary portion of the structure of FIGS. 1, 2 and 3.
Figure 12:
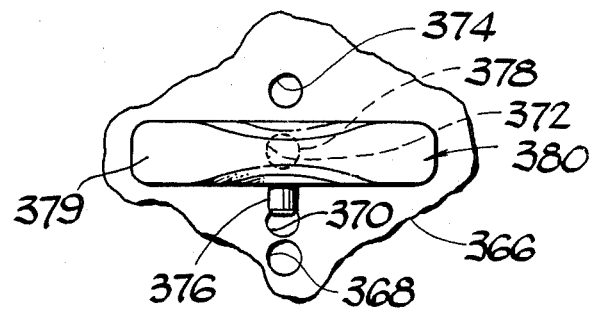
Figure 13:
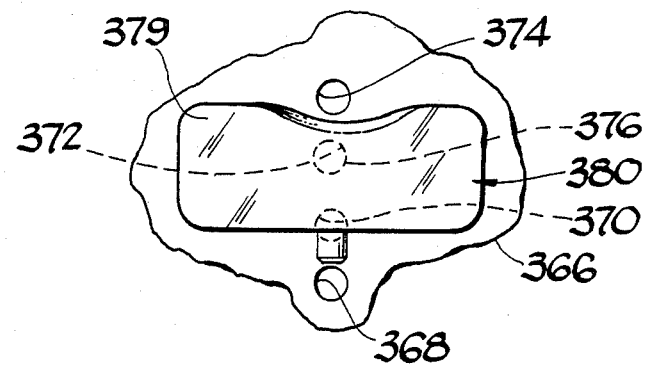

Further, in the preferred embodiment, a plurality of holes or passages 368, 370, 372 and 374 are preferably formed in support 366 as generally depicted in FIG. 1. Such holes are intended to receive either of peg or rod-like portions 376 and 378 of the body 379 of a neck rest 380 as generally depicted in FIGS. 11, 12 and 13. The plurality of holes or passages 368-374 in effect provide for adjustment due to the size of the patient's head while the choice of engaging either rod portion 376 or 378 will depend, primarily on the age of the patient and the degree of curvature of the back of the neck at the base of the skull. Obviously, if rod portion 378 is engaged, the height of rest body 379 is comparatively higher than if the side mounted rod portion 376 is engaged.

Although the practice of the invention is not so limited, in the preferred arrangement of the invention, elements 14, 16, 18, 26, 36, 300, 198, 114, 128, 184, 344 and 280 are formed of a clear plexiglass while, for example, a high molecular weight polyethylene is preferably used for the ways 52, 54, block 140 and trunnions or pivot supports 20 and 22. The various gears are commercially available as stock items and the respective ratios etc. would, in the main, be a matter of personal choice.

In the use of the invention, one film cassette of unexposed film could be retained as at 250 (vertically generally between clamp 202 and the top of base foot or rail 16). Further, in use, the invention is primarily intended to be set upon a table (or the like), portions of which are fragmentarily illustrated at 382 and 384. In such an arrangement, the height of the feet or risers 16 and 18 is such as to permit the very close reception, as between table surface 386 and the underside surface 180 of base plate 14, of a second film cassette 388 of unexposed film so that, for all practical purposes, the surface 180 will be the surface of the film to be exposed. Not only do the risers 16 and 18 provide for such a closely held vertical opening, but the inner sides thereof may well serve as longitudinal guides for the sliding guide of the film cassette being inserted therebetween.

As already indicated, the invention also provides for the additional placement of film cassettes containing film to be exposed. One such location is in the space between arm 324 and arm portion 252, as depicted in FIG. 1 and hereinbefore discussed. Another such location is to the right side of arm portion 330 (as viewed in FIG. 1), when arm 324 and retainer knob 320 are used in combination therewith, as also hereinbefore discussed and described. Further, as also previously described, the U-shaped portion 332 serves to provide for a still further location of a film cassette.

OPERATION OF INVENTION

Figure 14:
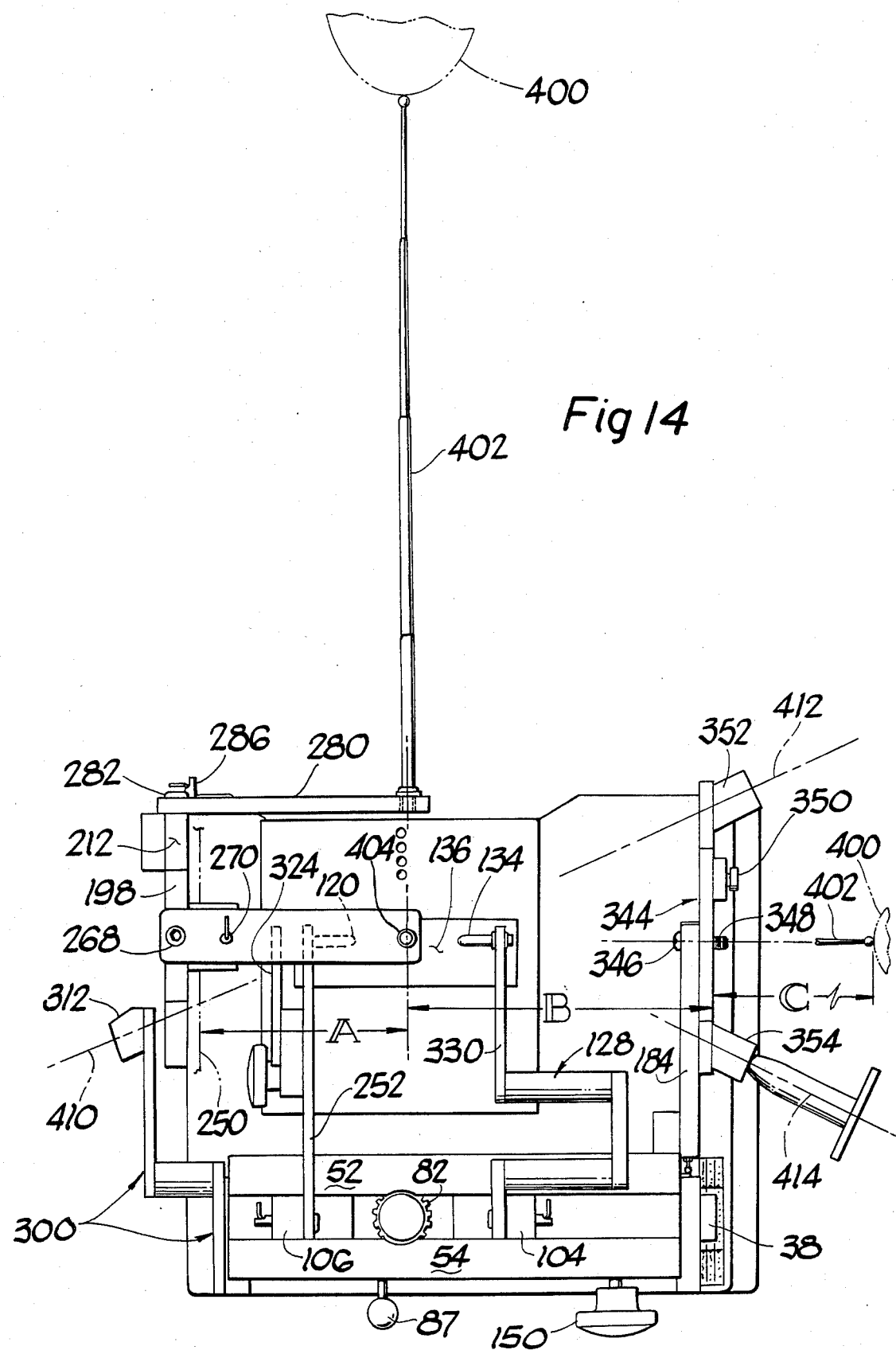
FIG. 14 is a view similar to that of FIG. 1, in reduced scale, and with considerably less detail, illustrating the apparatus of the invention as it may appear prior to the exposing of the unexposed film situated to the left of the patient's head.
Figure 15:
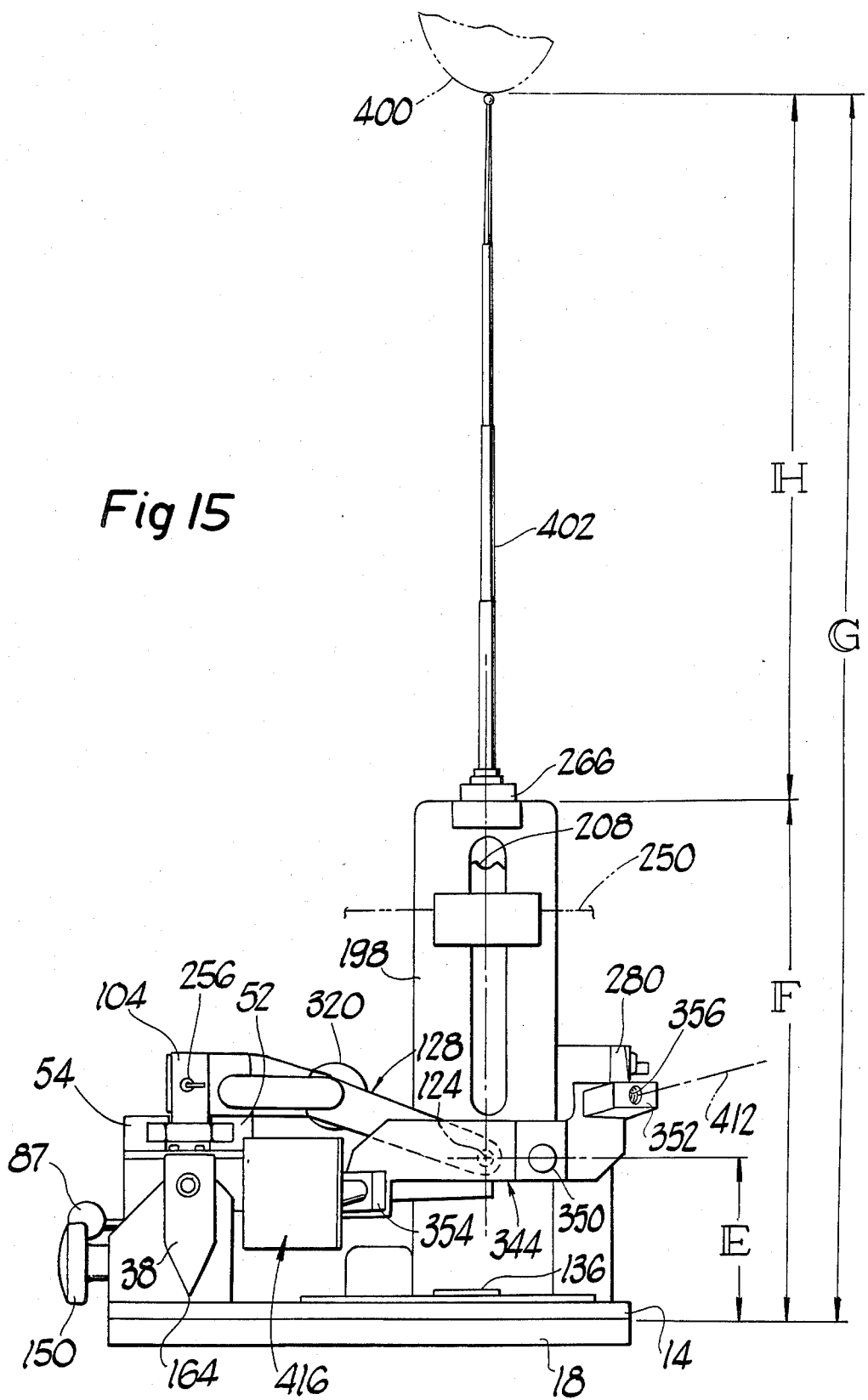
FIG. 15 is a view similar to that of FIG. 4, in reduced scale, and with considerably less detail, illustrating the apparatus of the invention as it may appear prior to the exposing of the unexposed film situated below the patient's head.

In order to better convey the operation of the invention in addition to FIGS. 1–13, reference will also be made to FIGS. 14 and 15.

FIGS. 14 and 15 are somewhat respectively similar to FIGS. 1 and 4 with the exceptions that FIGS. 14 and 15 are each of a relatively reduced scale and only so many of the elements (some somewhat comparatively simplistically illustrated) are shown as is believed necessary to convey the interrelationships thereof and the overall operation of the invention.

Referring in greater detail to FIGS. 14 and 15, in one successful embodiment of the invention, the mid-distance between the locating members 120 and 134 when measured to the plane of the cassette film to be exposed was established at a dimension, A, which, in the preferred embodiment was established to be 15.0 cm. Accordingly, after a patient's head is placed on the pad or riser 138 (preferably the elevation of which is sufficient to overcome the metal frame of the film cassette) as to have the back or posterior portion of that patient's head rest on surface 136, lever 87 is rotated in a direction as to cause the locating arms 114 and 128 as well as locating members 120 and 134 move relatively toward each other. The locating members 120 and 134 are in fact plug-like members adapted to be received in the external auditory canals, or porionic canals, of the patient. Therefore, such locating members 120 and 134 are moved generally inwardly toward the patient's auditory canals along with such adjustments as are necessary with knob 150 to place such locating members at the proper elevation to be received by the patient's auditory canals.

At this time certain factors are established; that is, the mid-sagittal plane of the patient has been established as existing parallel to the film in the cassette 250 (if such is actually being employed) and at a fixed dimension, A, away from the film of such cassette; the other is that the transporionic axis has also been established as being axially aligned with the axis 124 of the locating members 120 and 134 which is also coaxial with means 348 of arm locator member 184.

In order to obtain a lateral X-ray exposure of the patient's head, all that is necessary is to bring the anode 400 of the related, generally standard, X-ray machine into alignment with axis 124 and cycle such X-ray machine for the desired exposure time. However, in many instances, it is desired to establish a particular degree of magnification which will be again used in subsequent cephlograms especially for purposes of comparison. With the invention this becomes very simple. That is, since the dimension, A, is fixed, the selected degree of magnification becomes a simple matter of mathematics. That is, the distance A+B+C (the total distance from the plane of the film to the anode 400 of the X-ray machine) divided by the distance B+C will give the resulting degree of magnification. Therefore, in the invention, with dimensions, A, and, B, being fixed and determined it becomes a simple mathematical equation to determine the dimension, C, in order to achieve the desired degree of magnification. This can be achieved as by the use of a telescoping rod 402 which is extensible and preferably detachably securable to the arm 184 as at threaded member 348. That is, with the axis of pivot 348 being aligned with axis 124 and the fixed dimensions, A and B, being known, all that has to be done is to attach telescoping rod 402 and extend it until it attains the proper calculated length, C, and then bring the anode 400 of the X-ray machine into alignment with rod 402 and in touching engagement therewith after which the arm 184 and telescoping rod 402 are swung upwardly (counter-clockwise as viewed in FIG. 4) and the X-ray machine cycled for the appropriate time span thereby exposing the film in the cassette 250.

Somewhat similarly, once the patient's head has been located as described above, the graduations on gauge means 162 are checked to see which of such graduations is, for example, juxtaposed to the pointer 164. If, for example, the juxtaposed graduation is "12", that would mean that dimension, E, is actually 12.0 cm. away from the plane of the film in the cassette 388. If it is desired to establish a particular degree of magnification which will be again used in subsequent cephlograms especially for purposes of comparison, such becomes a very simple mathematical equation with the invention. That is, since dimension, E, is established by virtue of the rotation of the platform means 44 and locators 120, 134, and therefore for that patient at that time, fixed, the selected degree of magnification becomes a simple matter of mathematics. That is, the distance H and F (the total distance from the plane of the film to the anode of the X-ray machine) divided by the distance G-E will give the resulting degree of magnification. Therefore, in the invention with dimension, F, being fixed and dimension, E, being determinable, it becomes a simple mathematical equation to determine the dimension, H, in order to achieve the desired degree of magnification. This can be achieved as by the use of a telescoping rod 402 which is extensible and detachably securable to the arm 280 as at threaded stud means 404. That is, with the axis of stud 404 being aligned with the mid-sagittal plane and fixed dimension, F, being known, less the determinable dimension, E, all that has to be done is to attach telescoping rod 402 and extend it until it attains the proper calculated length, H, and then bring the anode 400 of the X-ray machine into alignment with rod 402 and in touching engagement therewith after which the arm 280 and telescoping rod 402 may be swung as to a position out of the line of action of the X-ray machine, and the X-ray machine cycled for the appropriate time span thereby exposing the film in the cassette 388.

FIG. 14 also depicts the use of the expandible or telescoping rod 402 detachably secured to arm 280 and positioned as to be in the mid-sagittal plane. Once the proper or desired distance to the X-ray anode 400 is determined, in the manner as generally hereinbefore described, the arm 280 and telescoping measuring rod 402 may be swung out of the line of radiation and the X-ray machine cycled for the appropriate exposure time. This, of course, would expose the film held generally beyond the top of the patient's head and contained by the U-shaped arm portion 332 of arm means 128. It should be pointed-out that in the preferred embodiment arm 280 is provided with three mounting apertures each of which is swingable into the mid-sagittal plane as the detent or plunger 288 is sequentially engaged within apertures or passages 290, 292 and 294. Each of such mounting apertures is effective to detachably carry the telescoping rod 402 for establishing the desired distance to the anode 400. However, each of such mounting apertures forms a slightly different, yet preselected, angle with respect to the horizontal thereby providing some preselected degree of latitude in the angle of the radiation with respect to the patient's head. In any event, this particular X-ray gives a view of structures in the patient's head looking through the vertical axis from under the chin to the top of the patient's head. It should be pointed out that the inclination of the measuring rod 402 is also an aid in avoiding any interference with the patient's body in bringing the anode 400 into position.

In FIGS. 14 and 15, centerlines or axis 410, 412 and 414 respectively represent the axis of apertures 314, 356 and 358, as shown, for example, in FIG. 1. Generally, each of such apertures 314, 356 and 358 may, sequentially, support the measuring or gauging rod 402 for purposes of establishing the direction of the X-ray and the selected distance of the anode 400. For example, if a left temporo-mandibular joint radiogram were desired, the line of action of the X-ray would be axis 414 and the film cassette would be situated as at 250, that is, against support 198. If a right temporo-mandibular joint radiogram were desired, the line of action of the X-ray would be axis 412 and the film cassette would be situated as between juxtaposed arms 324 and 252. A right temporo-mandibular joint radiogram can also be taken by positioning the anode 400 as to have the X-ray line of action along axis 410 and the film cassette would be situated against surface 342 and held there as by the repositioned arm 324 as previously discussed.

Among others, FIGS. 1, 5 and 14 illustrate an adapter member 416 which may be threadably engaged as with any of apertures 314, 356 and 358 as to establish a fixed distance, therefrom against which, as at end 418, the anode 400 may be brought for certain selected radiograms.

Figure 16:
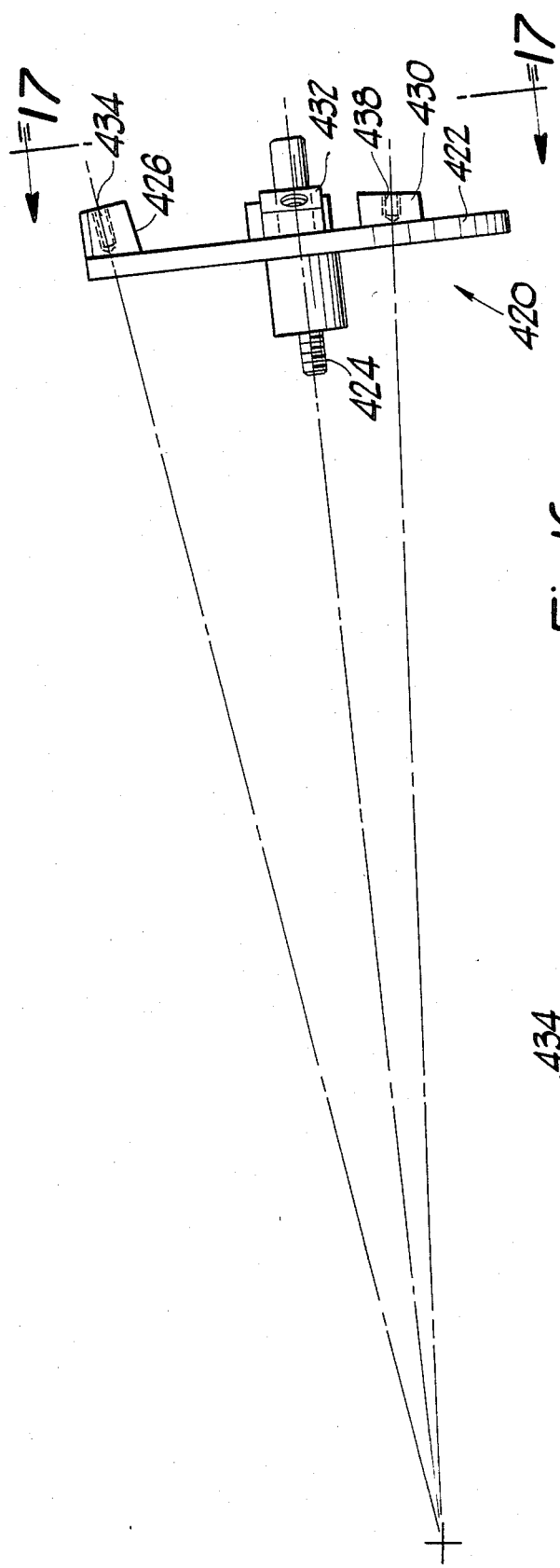
FIG. 16 illustrates in somewhat side elevational view one of the subassemblies employable in the practice of the invention.
Figure 17:
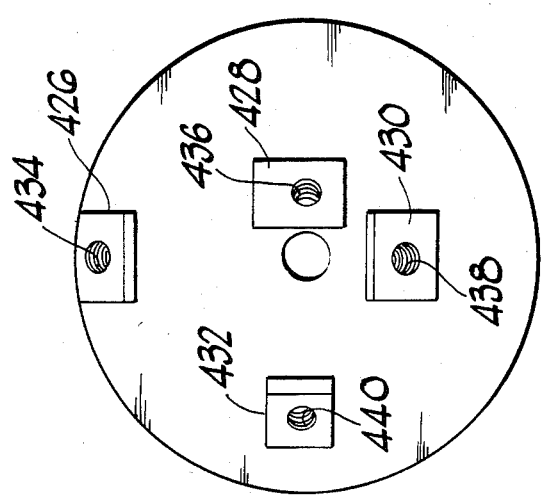
FIG. 17 is a view taken generally on the plane of line 17—17 of FIG. 16 and looking in the direction of the arrows.

FIGS. 16 and 17 illustrate another adapter 420 which may be employed as with any apertures 314, 356 and 358. Generally adapter 420 comprises a body 422 with a threaded stud 424 which can be threadably engaged with any of apertures 314, 356 and 358. The body, in turn, carries a plurality of body portions 426, 428, 430 and 432 with respective threaded apertures 434, 436, 438 and 440 the axes of which form differing angles as with respect to the axis 442 of stud 424. By first attaching the adapter 420 to, for example, aperture 356, the operator may select any of the threaded apertures 434, 436, 438 or 440 to which the gauging or measuring rod 402 would be attached for then positioning and aligning the anode 400. The selection of the particular aperture 434, 436, 438 or 440 will, of course, result in a different relative angle of the line of X-ray radiation which may be necessary in order to obtain a clear and sharp X-ray exposure especially where there may be a malformation in the structure of the patient's head being studied.

FIGS. 19, 20 and 21 illustrate a modified form of read-out means. That is, instead of the sweeping-like pointer 38, FIGS. 19, 20 and 21 contemplate the provision of right-angle type gear train means 442 operatively connected as to shaft 32 so that a rotatable output drum or cylindrical member 444 rotates in corresponding relationship to the rotation of platform means 44 about axis 118. The outer surface of the cylindrical member 444 is provided with a read-out scale 446 (which may be functionally equivalent to scale means 162) with, for example, three scales thereon each graduated in inches and/or centimeters. FIG. 18 illustrates such a scale 446 in a generally flat condition. A stationary pointer or indicator 448 serves to provide a read-out of the juxtaposed graduation on the scale 446 as it is rotated to a particular position.

Although only a preferred embodiment and certain modifications of the invention have been disclosed and described, it is apparent that other embodiments and modifications of the invention are possible within the scope of the appended claims.

What is claimed is:

1. A portable cephalostat, comprising portable body means, first means defining a non-resilient fixed reference plane of elevation carried by said body means and against which the back of a patient's head is to be directly located, second means for locating first unexposed film at a preselected elevation below the back of the patient's head and said fixed reference plane of elevation, third means for locating second unexposed film to one side of the patient's head when the back of said patient's head is located against said fixed reference plane of elevation, fourth means for locating third unexposed film at generally the top of the patient's head when the back of said patient's head is located against said fixed reference plane of elevation, and fifth means for guidingly positioning said patient's head along said fixed reference plane of elevation as to have the mid-sagittal plane of said patient's head situated at a preselected distance from said second unexposed film and for determining the elevation above the plane of said first film of the axis of said patient's auditory canals when the mid-sagittal plane of the patient's head is at said preselected distance, wherein said second means comprises reference surface means carried by said body means, wherein said third means comprises support means carried by said body means, wherein said support means is effective to support said second unexposed film in a generally vertical position generally parallel to said mid-sagittal plane, wherein said fifth means comprises first and second arm-like containing means, said first arm-like containing means being effective to be disposed at a first side of the patient's head, said second arm-like containing means being effective to be disposed at a second side of the patient's head opposite to said first side, first ear canal locating means carried by said first arm-like containing means and extending generally toward said second arm-like containing means, second ear canal locating means carried by said second arm-like containing means and extending generally toward said first arm-like containing means, said first and second arm-like containing means being adjustable through an arcuate path of movement simultaneously toward and away from said fixed reference plane of elevation as to enable said first and second ear canal locating means to be at an appropriate elevation with respect to said fixed reference plane of elevation as to enable the respective reception of said first and second ear canal locating means by the auditory canals of the patient's head, wherein said arcuate path of movement is about an axis of rotation, wherein said axis of rotation is parallel to said fixed reference plane of elevation, and said first and second arm-like containing means also being simultaneously movable toward and away from each other as to thereby respectively generally contain and release said patient's head.

2. A cephalostat according to claim 1 wherein said support means is foldable with respect to said body means.

3. A cephalostat according to claim 1 wherein one of said arm-like containing means comprises at least a portion of said fourth means.

4. A cephalostat according to claim 1 wherein said first and second arm-like containing means are also independently pivotally movable with respect to each other.

5. A cephalostat according to claim 4 and further comprising read-out type indicator means, said indicator means being effective to indicate the actual distance above said plane of said first film of the axis of the patient's auditory canals when the mid-sagittal plane of the patient's head is at said selected distance, and said indicator means being effective to continually indicate the changing distance as between said plane of said first film and said ear canal locating means as said first and second arm-like containing means are moved in said arcuate path.

6. A cephalostat according to claim 5 wherein said indicator means comprises movable arm-like pointer means and readable stationary characters, said characters as pointed to by said pointer means providing a visual indication of said distance above said plane of said first film.

7. A cephalostat according to claim 1 and further comprising manually operative drive means operatively connected to said first and second arm-like containing means and rotatable in unison with said first and second arm-like containing means about said axis of rotation as said first and second arm-like containing means are selectively moved in said arcuate path, said drive means being effective to cause said first and second arm-like containing means to simultaneously move toward or away from each other.

8. A cephalostat according to claim 7 wherein said manually operative drive means comprises rotary gear means, first gear rack means, second gear rack means, wherein said first gear rack means is in meshed engagement with said rotary gear means at generally one diametral side of said rotary gear means, wherein said second gear rack means is in meshed engagement with said rotary gear means at generally a second diametral side of said rotary gear means generally opposite to said one diametral side, wherein said first gear rack means is operatively connected to said first arm-like containing means, wherein said second gear rack means is operatively connected to said second arm-like containing means, and wherein upon manual rotation of said rotary gear means said first and second gear rack means are caused to move in directions opposite to each other.

9. A portable cephalostat, comprising portable body means, first means defining a non-resilient fixed reference plane of elevation carried by said body means and against which the back of a patient's head is to be located, second means for locating first unexposed film at a selected elevation below the back of the patient's head and said fixed reference plane of elevation, third means for locating second unexposed film to one side of the patient's head when the back of said patient's head is operatively located against said fixed reference plane of elevation, and fourth means for guidingly positioning said patient's head along said fixed reference plane of elevation as to have the mid-sagittal plane of said patient's head situated at a selected distance from said second unexposed film and for determining the elevation above the plane of said first film of the axis of said patient's auditory canals when the mid-sagittal plane of the patient's head is at said selected distance, said third means being movable as to be horizontally positionable with respect to said reference plane of elevation, wherein said fourth means comprises first and second arm-like containing means, said first arm-like containing means being effective to be disposed at a first side of the patient's head, said second arm-like containing means being effective to be disposed at a second side of the patient's head opposite to said first side, first ear canal locating means carried by said first arm-like containing means and extending generally toward said second arm-like containing means, second ear canal locating means carried by said second arm-like containing means and extending generally toward said first arm-like containing means, said first and second arm-like containing means being adjustable through an arcuate path of movement simultaneously toward and away from said fixed reference plane of elevation as to enable said first and second ear canal locating means to be at an appropriate elevation with respect to said fixed reference plane of elevation as to enable the respective reception of said first and second ear canal locating means by the auditory canals of the patient's head, wherein said arcuate path of movement is about an axis of rotation, wherein said axis of rotation is parallel to said fixed plane of elevation, means for continuously indicating the elevation of said first and second ear canal locating means while said first and second arm-like containing means move through said arcuate path, and said first and second arm-like containing means also being simultaneously movable toward and away from each other as to thereby respectively generally contain and release said patient's head.

10. A portable cephalostat, comprising portable body means, first means for locating the back of a patient's head at a reference plane of elevation, second means for locating first unexposed film at a selected elevation below the back of the patient's head and said plane of elevation, third means for locating second unexposed film to one side of the patient's head when the back of said patient's head is operatively located against said reference plane of elevation, and fourth means for guidingly positioning said patient's head along said reference plane of elevation as to have the mid-sagittal plane of said patient's head situated at a selected distance from said second unexposed film and for determining the elevation above the plane of said first film of the axis of said patient's auditory canals when the mid-sagittal plane of the patient's head is at said selected distance, said third means being movable as to be horizontally positionable with respect to said reference plane of elevation, wherein said third means comprises support means operatively carried by said body means, and wherein said support means is effective to support said second unexposed film in a generally vertical position generally parallel to said mid-sagittal plane, pivot means having a pivotal axis, wherein said pivotal axis is fixed against movement in a direction transverse to said pivotal axis, said support means being operatively pivotally connected to said body means through said pivot means, and manually actuatable latching means for at times latchingly locking said support means in said generally vertical position.

11. A portable cephalostat, comprising portable body means, first means for locating the back of a patient's head at a reference plane of elevation, second means for locating first unexposed film at a selected elevation below the back of the patient's head and said plane of elevation, third means for locating second unexposed film to one side of the patient's head when the back of said patient's head is operatively located against said reference plane of elevation, and fourth means for guidingly positioning said patient's head along said reference plane of elevation as to have the mid-sagittal plane of said patient's head situated at a selected distance from said second unexposed film and for determining the elevation above the plane of said first film of the axis of said patient's auditory canals when the mid-sagittal plane of the patient's head is at said selected distance, said third means being movable as to be horizontally positionable with respect to said reference plane of elevation, wherein said fourth means comprises first and second arm-like means, first ear canal locating means operatively carried by said first arm-like means and extending generally toward said second arm-like means, second ear canal locating means operatively carried by said second arm-like means and extending generally toward said first arm-like means, said first and second arm-like means being adjustable relative to said reference plane of elevation as to enable said first and second ear canal locating means to be respectively operatively received by the auditory canals of the patient's head, and wherein said second arm-like means comprises an eccentrically situated locating means effective for locating associated film means to be exposed.

12. A portable cephalostat, comprising portable body means, first means for locating the back of a patient's head at a reference plane of elevation, second means for locating first unexposed film at a selected elevation below the back of the patient's head and said plane of elevation, third means for locating second unexposed film to one side of the patient's head when the back of said patient's head is operatively located against said reference plane of elevation, and fourth means for guidingly positioning said patient's head along said reference plane of elevation as to have the mid-sagittal plane of said patient's head situated at a selected distance from said second unexposed film and for determining the elevation above the plane of said first film of the axis of said patient's auditory canals when the mid-sagittal plane of the patient's head is at said selected distance, said third means being movable as to be horizontally positionable with respect to said reference plane of elevation, wherein said fourth means comprises first and second arm-like means, first ear canal locating means operatively carried by said first arm-like means and extending generally toward said second arm-like means, second ear canal locating means operatively carried by said second arm-like means and extending generally toward said first arm-like means, said first and second arm-like means being adjustable relative to said reference plane of elevation as to enable said first and second ear canal locating means to be respectively operatively received by the auditory canals of the patient's head, and additional third fourth fifth and sixth arm-like means, said additional arm-like means serving to align the axis of X-ray radiation of associated X-ray apparatus.

13. A portable cephalostat; comprising portable body means, first means defining a non-resilient fixed reference plane of elevation carried by said body means and against which the back of a patient's head is to be located, second means for locating first unexposed film at a preselected elevation below the back of the patient's head and said fixed reference plane of elevation, third means for locating second unexposed film to one side of the patient's head when the back of said patient's head is operatively located against said fixed reference plane of elevation, fourth means for guidingly containing said patient's head when said patient's head is located against said fixed reference plane of elevation as to thereby have the mid-sagittal plane of said patient's head situated at a preselected distance from said second unexposed film and for determining the elevation above said plane of said first film of said patient's auditory canals when the mid-sagittal plane of the patient's head is at said preselected distance from said second unexposed film, wherein said fourth means comprises first and second arm-like containing means, said first arm-like containing means being effective to be disposed at a first side of the patient's head, said second arm-like containing means being effective to be disposed at a second side of the patient's head opposite to said first side, first ear canal locating means operatively carried by said first arm-like containing means and extending generally toward said second arm-like containing means, second ear canal locating means operatively carried by said second arm-like containing means and extending generally toward said first arm-like containing means, said first and second arm-like containing means being simultaneously movable toward and away from each other as to respectively generally contain and release said patient's head, said first and second arm-like containing means also being selectively movable in unison in an arcuate path toward and away from said fixed reference plane of elevation so that said first and second ear canal locating means may be positioned at an elevation with respect to said fixed reference plane of elevation as to be made simultaneously respectively aligned with and receivable by the auditory canals of the patient's head, wherein said arcuate path has a center of rotation, manually operative drive means operatively connected to said first and second arm-like containing means, support means for said drive means, said support means and said drive means being rotatable in unison with said first and second arm-like containing means about said center of rotation as said first and second arm-like containing means are selectively moved in said arcuate path, said drive means being effective to cause said first and second arm-like containing means to simultaneously move toward or away from each other, said manually operative drive means comprising rotary gear means, first gear rack means, second gear rack means, wherein said first gear rack means is in meshed engagement with said rotary gear means at generally one diametral side of said rotary gear means, wherein said second gear rack means is in meshed engagement with said rotary gear means at generally a second diametral side of said rotary gear means generally opposite to said one diametral side, wherein said first gear rack means is operatively connected to said first arm-like containing means, wherein said second gear rack means is operatively connected to said second arm-like containing means, wherein upon manual rotation of said rotary gear means said first and second gear rack means are caused to move in directions opposite to each other, fourth arm-like means, and fifth arm-like means, said fourth and fifth arm-like means being operatively connected to said support means as to be rotatable in unison with said support means with said drive means and said fifst and second arm-like containing means about said center of rotation, said fourth arm-like means comprising first aiming means for aiming the axis of radiation of an associated X-ray source at an angle which is skew to a transporionic axis cooperatively determined by said first and second ear canal locating means, and said fifth arm-like means comprising second aiming means for aiming the axis of radiation of an associated X-ray source at an angle which is skew to said transporionic axis, said fourth arm-like means being situated as to be disposed generally on one side of said patient's head when the back of said patient's head is operatively against said fixed reference plane of elevation, and said fifth arm-like means being situated as to be disposed generally on the other side of said patient's head opposite to said one side.

14. A portable cephalostat according to claim 13 wherein said first and second arm-like containing means are independently pivotally movable with respect to each other.

15. A portable cephalostat according to claim 13 wherein said second aiming means comprises third and fourth aiming means, wherein each of said third and fourth aiming means is effective for aiming the axis of radiation of said associated X-ray source at an angle which is skew to said transporionic axis, and wherein said third and fourth aiming means are not in axial alignment with each other.

16. A portable cephalostat according to claim 15 wherein said fifth arm-like means comprises first and second lever-like means, wherein said first lever-like means is operatively connected to said support means for rotation therewith, additional pivot means carried by said first lever-like means, wherein said second lever-like means is operatively connected to said first lever-like means through said additional pivot means, and wherein said third aiming means is carried by said second lever-like means at a location which is in a first radial direction away from said additional pivot means, and wherein said fourth aiming means is carried by said second lever-like means at a location which is in a second radial direction away from said additional pivot means generally opposite to said first radial direction.

* * * * *

UNITED STATES PATENT AND TRADEMARK OFFICE
CERTIFICATE OF CORRECTION

PATENT NO.  : 4,683,582

DATED       : July 28, 1987

INVENTOR(S) : John L. Spolyar

It is certified that error appears in the above-identified patent and that said Letters Patent is hereby corrected as shown below:

Column 4, line 34, change "6" to --- 66 ---.

Column 4, line 37, change "4" to --- 64 ---.

Column 7, line 16, change --- "938 ---
    to --- "9" ---.

Column 10, line 16, change "mids-agittal" to
    --- mid-sagittal ---.

Column 20, line 17 thereof, change "fifst" to --first --.

Signed and Sealed this

Sixteenth Day of February, 1988

*Attest:*

DONALD J. QUIGG

*Attesting Officer*   *Commissioner of Patents and Trademarks*